United States Patent
Joshi

(10) Patent No.: US 8,594,804 B2
(45) Date of Patent: Nov. 26, 2013

(54) IMPLANTABLE MEDICAL DEVICE CHARGING

(75) Inventor: Himanshu Joshi, Houston, TX (US)

(73) Assignee: Cyberonics, Inc., Houston, TX (US)

( * ) Notice: Subject to any disclaimer, the term of this patent is extended or adjusted under 35 U.S.C. 154(b) by 275 days.

(21) Appl. No.: 13/096,805

(22) Filed: Apr. 28, 2011

(65) Prior Publication Data
US 2012/0277831 A1    Nov. 1, 2012

(51) Int. Cl.
*A61N 1/00* (2006.01)

(52) U.S. Cl.
USPC .......................................................... 607/61

(58) Field of Classification Search
USPC .......................................................... 607/61
See application file for complete search history.

(56) References Cited

U.S. PATENT DOCUMENTS

| | | | |
|---|---|---|---|
| 4,665,896 A | 5/1987 | LaForge et al. | |
| 5,154,172 A | 10/1992 | Terry, Jr. et al. | |
| 5,222,494 A | 6/1993 | Baker, Jr. | |
| 5,350,413 A * | 9/1994 | Miller | 607/61 |
| 6,240,318 B1 * | 5/2001 | Phillips | 607/61 |
| 6,516,227 B1 | 2/2003 | Meadows et al. | |
| 6,972,543 B1 | 12/2005 | Wells | |
| 7,177,691 B2 | 2/2007 | Meadows et al. | |
| 7,729,760 B2 | 6/2010 | Patel et al. | |
| 7,751,891 B2 | 7/2010 | Armstrong et al. | |
| 7,769,466 B2 | 8/2010 | Denker et al. | |
| 2005/0075697 A1 | 4/2005 | Olson et al. | |
| 2006/0247737 A1 | 11/2006 | Olson et al. | |
| 2009/0210035 A1 | 8/2009 | Gelbart | |
| 2010/0137948 A1 * | 6/2010 | Aghassian et al. | 607/61 |
| 2011/0046699 A1 * | 2/2011 | Mazanec | 607/61 |
| 2012/0262108 A1 | 10/2012 | Olson | |

OTHER PUBLICATIONS

Yungtaek Jang et al., "A Contactless Electrical Energy Transmission System for Portable-Telephone Battery Chargers," IEEE Transactions on Industrial Electronics, vol. 50, No. 3, Jun. 2003, pp. 520-527.
Sung-Noon Cho et al., "A Wireless Powered Fully Integrated SU-8-Based Implantable LC Transponder," Technical Paper, Microsyst Technol, Springer-Verlag 2010, Received Jul. 17, 2009, Accepted Feb. 16, 2010, Published Online, Mar. 9, 2010, 7 pages.
Gurhan Alper Kendir et al., "An Optimal Design Methodology for Inductive Power Link with Class-E Amplifier," IEEE Transactions on Circuits and Systems—I: Regular Papers, vol. 52, No. 5, May 2005, pp. 857-866.
International Application No. PCT/US2012034150, PCT International Search Report and Written Opinion dated Oct. 5, 2012, 11 pages.

* cited by examiner

*Primary Examiner* — Christopher D Koharski
*Assistant Examiner* — Philip Edwards
(74) *Attorney, Agent, or Firm* — Cyberonics, Inc.

(57) ABSTRACT

A particular method of providing power to an implantable medical device includes providing a first signal to a primary coil that is inductively coupled to a secondary coil of an implantable medical device. The method also include determining a first alignment difference between a voltage corresponding to the first signal and at least one of a current corresponding to the first signal and a component voltage at a component of a primary coil circuit. The method further includes determining a frequency sweep range based on the first alignment difference. The method also includes performing a frequency sweep over the frequency sweep range.

27 Claims, 8 Drawing Sheets

IMPLANTABLE MEDICAL DEVICE CHARGING

FIELD OF THE DISCLOSURE

The present disclosure is generally related to implantable medical devices.

BACKGROUND

Advances in technology have led to the development of miniature medical devices that can be implanted within a living organism, such as a human, to provide treatment or monitoring. Powering such implantable medical devices can be a concern. For example, some implantable medical devices use an onboard battery as a power source. However, since batteries store a finite amount of energy, an onboard battery may only be a temporary power source. Replacing batteries for implantable medical devices may be expensive and inconvenient. For example, depending on the specific nature of the implantable medical device, surgery may be needed to replace the device or to replace the battery.

Due to these and other concerns, some implantable medical devices may use rechargeable batteries. However, recharging batteries that are located inside a device that is implanted in a patient presents other concerns. For example, when long charging times are required, patient compliance can be a problem. As another example, inefficient recharging may cause energy to be lost as heat. Such heat losses may dissipate into surrounding tissues, which may be harmful to the patient.

SUMMARY

A battery onboard an implantable medical device can be recharged using an inductively-coupled recharging system. For example, a recharging device that is external to a patient may include a power circuit coupled to a primary coil. The implantable medical device (internal to the patient) may include a recharging circuit coupled to a secondary coil. The primary and secondary coils may be inductively coupled to enable transfer of energy from the primary coil to the secondary coil. The recharging circuit may provide energy received by the secondary coil from the primary coil to a battery. Thus, the inductively-coupled recharging system enables the battery to be wirelessly recharged from a source external to the patient via the inductive coupling of the primary and secondary coils.

Heat losses of the implantable medical device can be reduced by reducing resistive heating. Resistive losses in an RLC circuit, such as the power circuit and the recharging circuit, can be reduced by operating the RLC circuit at its resonant frequency. However, the resonant frequency of the inductively-coupled recharging system can be difficult to determine and can change dynamically. For example, minor variations in the circuits (e.g., from one implantable medical device to another implantable medical device) can change the resonant frequency. Other variations, such as position or orientation differences between the primary coil and the secondary coil, can also affect energy transfer efficiency.

To address such concerns, an alignment relationship may be determined to determine whether the signal is provided at the resonant frequency of the power circuit. For example, the alignment relationship may be determined by evaluating voltage and current of a signal applied to the primary coil. The voltage and the current of the signal are aligned (e.g., in phase) when a frequency of the signal is at the resonant frequency of the inductively-coupled recharging system. Phase differences between the current and the voltage of the signal can be used to estimate the resonant frequency. For example, when the voltage is lagging the current, the resonant frequency of the inductively-coupled recharging system is higher than the frequency of the signal. Alternately, when the voltage leads the current, the resonant frequency of the inductively-coupled recharging system is lower than the frequency of the signal. Thus, in a particular embodiment, the inductively-coupled recharging system can be controlled to reduce heating and to improve recharging efficiency based on measurements of the phase difference between the voltage and the current of the signal provided to the primary coil.

Further improvement of the efficiency of energy transfer may be achieved by monitoring parameters of the recharging circuit. For example, a voltage applied to the battery by the recharging circuit within the implantable medical device may be monitored. For a particular duty cycle of the signal applied to the primary coil, the voltage applied to the battery may be greatest when the signal is at the resonant frequency of the inductively-coupled recharging system. A frequency sweep may used to identify the resonant frequency. The frequency sweep may be performed by applying signals of different frequencies to the primary coil while measuring the voltage applied to the battery by the recharging circuit within the implantable medical device. A range of frequencies to be swept by the frequency sweep may be determined based on the phase difference between the current and the voltage at a particular frequency. For example, when a first signal is applied to the primary coil, the phase difference between the current and the voltage of the first signal may be determined. A frequency sweep range may be selected based on the phase difference. To illustrate, a direction to change the frequency relative to the first frequency may be determined based on a sign of the phase difference. In addition, a magnitude of a frequency change from the first signal to a particular portion of the frequency sweep (e.g. a midpoint of the frequency sweep range) may be selected based on a magnitude of the phase difference.

After the resonant frequency has been determined (within a threshold), a recharging signal having the resonant frequency may be provided to the primary coil. Additionally, a duty cycle of the recharging signal may be increased to increase a rate of energy transfer to the implantable medical device. Thus, heating losses during battery recharging may be reduced, improving patient safety. The energy transfer rate also may be improved (by reducing losses and by increasing the duty cycle at the resonant frequency) which may improve patient compliance with recharging the battery since battery recharge time may be shortened.

In a particular embodiment, a method of controlling power delivery to an implantable medical device includes providing a first signal to a primary coil that is inductively coupled to a secondary coil of an implantable medical device. The method also includes determining a first alignment difference between a voltage corresponding to the first signal and at least one of a current corresponding to the first signal and a component voltage at a component of a primary coil circuit. The method further includes determining a frequency sweep range based on the first alignment difference. The method also includes performing a frequency sweep over the frequency sweep range.

In a particular embodiment, a device includes a primary coil coupled to a circuit and operable to inductively couple to a secondary coil within an implantable medical device to transfer energy to the secondary coil within the implantable medical device responsive to a signal of the circuit. The device also includes a sensing system coupled to the circuit.

The sensing system is operable to detect an indication of an alignment relationship between a voltage corresponding to the signal and at least one of a current corresponding to the signal and a component voltage at a component of the circuit. The system also includes a control system responsive to the sensing system. The control system is operable to determine a frequency sweep range based on the alignment relationship and to cause the primary coil to receive a charging signal having a frequency within the frequency sweep range during the transfer of the energy.

In a particular embodiment, an implantable medical device includes a secondary coil coupled to a circuit and operable to inductively couple to a primary coil to receive energy from the primary coil. The implantable medical device also includes a battery charging system coupled to the secondary coil and operable to receive a current from the secondary coil and to apply a charging voltage to a battery responsive to the current. The implantable medical device further includes a measurement system coupled to the circuit and operable to measure an electrical property of the circuit and to output information indicative of a value of the electrical property. The secondary coil is operable to receive a charging signal from the primary coil. A frequency of the charging signal is determined based on the information indicative of the value of the electrical property and based on a detected alignment relationship between a voltage corresponding to a signal applied to the primary coil and at least one of a current corresponding to the signal and a component voltage at a component associated with the primary coil.

The features, functions, and advantages that have been described can be achieved independently in various embodiments or may be combined in yet other embodiments, further details of which are disclosed with reference to the following description and drawings.

DETAILED DESCRIPTION

Figure 1:
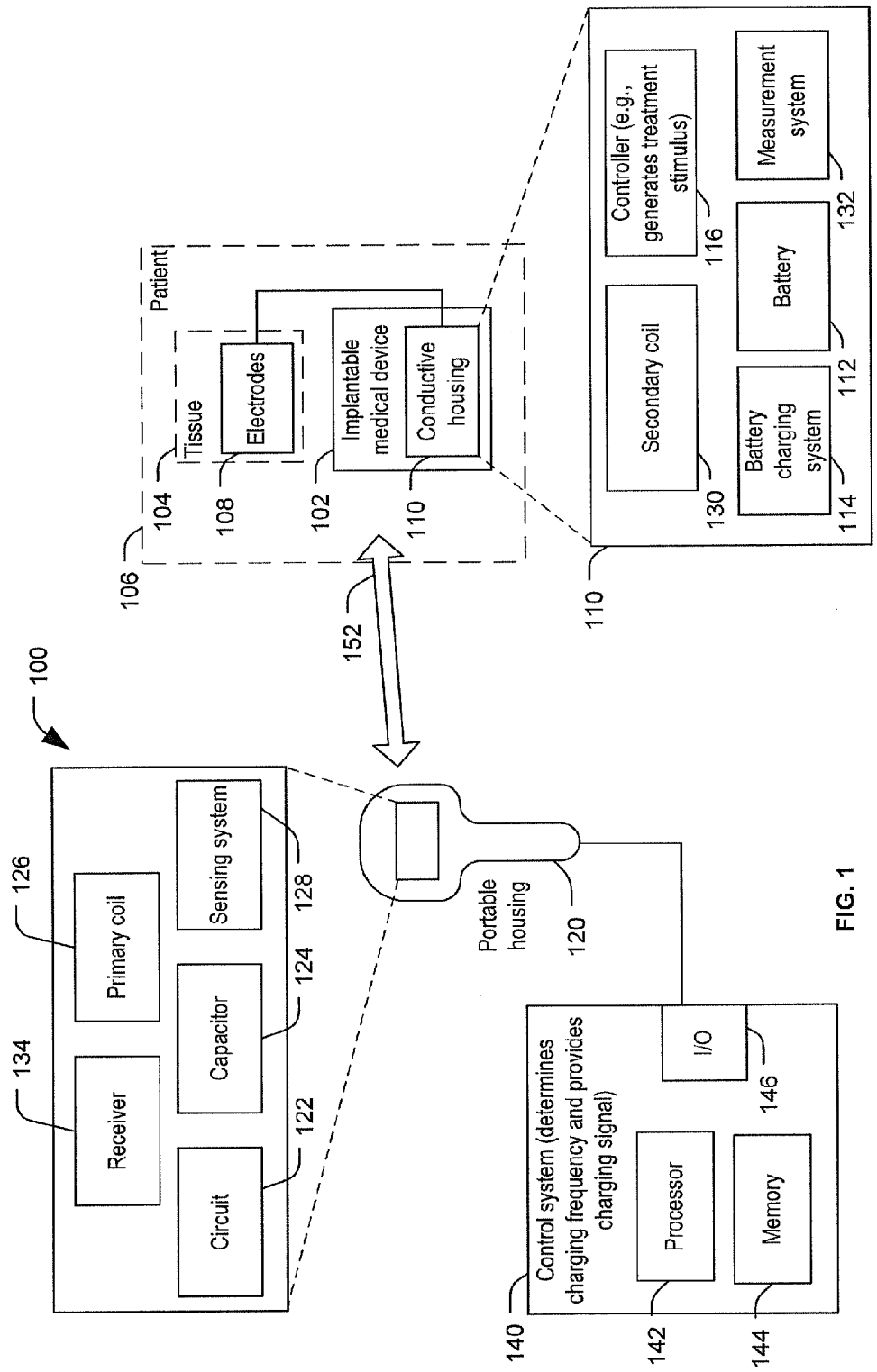
FIG. 1 is a block diagram of a particular embodiment of an implantable medical device and a charging system.

FIG. 1 is a block diagram of a particular embodiment of an implantable medical device 102 and an external charging system 100. The implantable medical device 102 may be adapted to be surgically implanted in a patient 106 to provide therapy, to monitor one or more conditions, for another purpose, or any combination thereof. In a particular embodiment, the implantable medical device 102 may be coupled to one or more electrodes 108 and may be adapted to deliver electrical stimulus to tissue 104 of the patient 106 via the electrodes 108. For example, the implantable medical device 102 may be a nerve stimulation device. The electrodes 108 may coupled to the implantable medical device 102 and may be positioned proximate to or coupled to a nerve, such as a cranial nerve (e.g., the trigeminal nerve, the hypoglossal nerve, the vagus nerve or a branch of the vagus nerve). The implantable medical device 102 may include a controller 116 that is operable to control generation of treatment stimulus provided to the electrodes 108 to provide an electrical stimulus to the tissue 104. Note that the term "patient" is used broadly to include any organism and is not intended to imply that the patient 106 is human; although the patient 106 is a human patient in one embodiment.

In a particular embodiment, the implantable medical device 102 may include a power supply, such as a battery 112, that stores power to operate the implantable medical device 102. The implantable medical device 102 may also include a battery charging system 114 that is operable to receive power from the external charging system 100 to recharge the battery 112. For example, the external charging system 100 may include a primary coil 126 that is operable to inductively couple 152 to a secondary coil 130 within the implantable medical device 102. The primary coil 126 may transfer energy to the secondary coil 130 responsive to a charging signal applied to a circuit 122 of the external charging system 100 that includes or is coupled to the primary coil 126. The battery charging system 114 may be coupled to the secondary coil 130 and may be operable to receive a current from the secondary coil 130 (responsive to the charging signal) and to apply a charging voltage to the battery 112 responsive to the current.

In a particular embodiment, the implantable medical device 102 may include a conductive housing 110. One or more of the battery 112, the battery charging system 114, the secondary coil 130, and other components of the implantable medical device 102 may be enclosed in the conductive housing 110. During recharging of the battery 112, the temperature of the conductive housing 110 may increase due to inductive coupling of the primary coil 126 with the conductive housing 110. To avoid damage to or discomfort of the patient 106, a temperature rise of the conductive housing 110 may be limited to a threshold. Accordingly, the external charging system 100 and the implantable medical device 102 may be adapted to recharge the battery 112 in a manner that limits heat dissipation and therefore limits the temperature increase of the conductive housing 110. In various particular embodiments, during recharging of the battery 112, the temperature of the conductive housing 110 may increase no more than 5 degrees Fahrenheit, no more than 4 degrees Fahrenheit, no more than 3 degrees Fahrenheit, no more than 2 degrees Fahrenheit, no more than 1 degree Fahrenheit, or less than 1 degree Fahrenheit.

One way to reduce dissipating energy as heat may be to provide a charging signal to the primary coil 126 at a resonant frequency of the circuit 122. The circuit 122 may include or be coupled to a capacitor 124; thus, the circuit 122 may be a resistive, inductive, capacitive circuit (also known as an RLC circuit). One characteristic of RLC circuits is that impedance of the circuit may be minimized when a signal applied to the RLC circuit is at a resonant frequency of the RLC circuit. Another way to reduce dissipating energy as heat may be to reduce a duty cycle of the signal applied to the primary coil 126 when a frequency of the signal is not at the resonant frequency of the circuit 122. That is, when energy provided via the signal is subject to higher heat losses (i.e., when the frequency of the signal is not at the resonant frequency of the circuit 122), the energy provided to the circuit 122 may be reduced by reducing the duty cycle of the signal, thus reducing energy available to be dissipated.

In a particular embodiment, the resonant frequency of the circuit 122 may be subject to change. For example, the resonant frequency of the circuit 122 may change based on the inductive coupling 152 of the primary coil 126 and the secondary coil 130. To illustrate, as the inductive coupling 152 of the coils 126, 130 changes, an effective inductance of the primary coil 126 may change. Stated another way, changing the inductive coupling 152 may change an apparent inductance of the primary coil 126 thereby changing the resonant frequency of the circuit 122. The inductive coupling 152 may change as a result of relative motion of the coils 126, 130, as a result of changes in the battery charging system 114 (e.g., increasing voltage of the battery 112), due to other causes, or any combination thereof.

The external charging system 100 may include a control system 140. The control system 140 may control application of signals to the primary coil 126. The control system 140 may include one or more processors, such as a processor 142, and memory accessible to the processor 142, such as a memory 144. The memory 144 may include tangible, non-transitory, computer-readable media (e.g., one or more computer memory devices). The processor 142 may be implemented using a single-chip processor or using multiple processors. The memory 144 may include various memory devices, such as registers, cache, volatile memory, and non-volatile memory. For example, the memory 144 can include cache that is accessible by the processor 142 to rapidly retrieve and store data. The memory 144 can include any data storage device that can store data which can thereafter be read by the control system 140 or by another computing system. Examples of computer-readable media that the memory 144 may use include, but are not limited to: magnetic media such as hard disks, floppy disks, and magnetic tape; optical media such as CD-ROM disks; magneto-optical media; and specially configured hardware devices such as application-specific integrated circuits (ASICs), programmable logic devices (PLDs), and ROM and RAM devices.

The memory 144 may store instructions that are executable by the processor 142 to implement various functions of the control system 140. To illustrate, the instructions may be executable by the processor 142 to control signals applied to the primary coil 126, to process information received from the implantable medical device 102, and so forth. Additionally or in the alternative, the control system 140 may include dedicated hardware implementations, such as application specific integrated circuits, programmable logic arrays and other hardware devices, to implement one or more functions of the control system 140. Accordingly, the present disclosure encompasses software, firmware, and hardware implementations.

The control system 140 may also include an input/output (I/O) interface 146. The I/O interface 146 may enable the control system 140 to send and receive information and signals to other components of the external charging system 100. For example, the circuit 122 and the primary coil 126 (as well as one or more other components) may be housed within a portable housing 120, such as a handheld wand or other device. The control system 140 may send control information and signals to the portable housing 120 via the I/O interface 146 and may receive information from the portable housing 120 via the I/O interface 146.

In a particular embodiment, the external charging system 100 may include a sensing system 128 coupled to the circuit 122. The sensing system 128 may be operable to detect information indicating that a signal applied to the circuit 122 is at a resonant frequency of the circuit 122. For example, the sensing system 128 may be operable to detect an indication of an alignment relationship between a voltage corresponding to the signal and a current corresponding to the signal. Additionally or in the alternative, the sensing system 128 may be operable to detect an indication of an alignment relationship between the voltage corresponding to the signal and a component voltage at a component of the circuit 122 (e.g., the capacitor 124 or the primary coil 126). The voltage corresponding to the signal and the current corresponding to the signal may be aligned (e.g., in phase) when the frequency of the signal is the resonant frequency of the circuit 122. The voltage corresponding to the signal and the component voltage at the component of the circuit 122 may be aligned (e.g., in phase) or offset by a predetermined offset amount, depending on the particular component of the circuit 122 across which the component voltage is measured, when the frequency of the signal is the resonant frequency of the circuit 122. The sensing system 128 may detect various information indicating the alignment relationships, as described further with reference to FIGS. 4-13. In a particular embodiment, the control system 140 may be responsive to the sensing system 128 to control application of signals to the primary coil 126.

The external charging system 100 may include a receiver 134 operatively coupled to the control system 140. The receiver 134 may be operable to receive information from the implantable medical device 102. For example, the receiver 134 may receive information that is indicative of an electrical property associated with the implantable medical device 102 or an electrical property associated with a component of the implantable medical device 102, such as the battery 112, the battery charging system 114, another component of the implantable medical device 102, or any combination thereof. For example, the implantable medical device 102 may include a measurement system 132. The measurement system 132 may measure the electrical property of the implantable medical device 102 or of the component of the implantable medical device 102, and output the information indicative of the electrical property to the receiver 134. To illustrate, the information may be sent by modulating a signal of the secondary coil 130. In an illustrative embodiment, the electrical property measured by the measurement system 132 may include a charge level of the battery 112, a voltage or current applied to the battery 112 by the battery charging system 114, another indication of an amount of power applied by the battery charging system 114 to the battery 112, another electrical property of a component of the implantable medical device 102, or any combination thereof.

The control system 140 may modify the signal applied to the primary coil 126 responsive to the information received from the implantable medical device 102. For example, when the information received from the implantable medical device 102 indicates that a voltage applied to the battery 112 by the battery charging system 114 satisfies a charging threshold, the control system 140 may modify a duty cycle of a charging signal applied to the primary coil 126. The charging threshold may be set at a level that is high enough to drive efficient charging of the battery 112. To illustrate, when the information received from the implantable medical device 102 indicates that the voltage applied to the battery 112 is sufficient to efficiently charge the battery 112, the control system 140 may increase the duty cycle of the charging signal (while maintaining a frequency of the charging signal) in order to increase a rate of charging of the battery.

In a particular embodiment, the control system 140 may control signals applied to the primary coil 126 to select a frequency of the charging signal. For example, the control system 140 may be operable to perform one or more frequency sweeps to select the frequency of the charging signal. The frequency of the charging signal may be selected to approximately correspond to the resonant frequency of the circuit 122 at a particular time (e.g., while the primary coil 126 and the secondary coil 130 have a particular spatial relationship, while the battery 112 has a particular charge level etc.). The frequency of the charging signal may be changed from time to time as conditions change. For example, when the portable housing 120 is moved, or when the patient 106 moves, the inductive coupling 152 may change, and the control system 140 may select a new frequency of the charging signal in response to the change. While the control system 140 is selecting a new frequency of the charging signal (e.g., during a frequency sweep), the duty cycle of the signal applied to the primary coil 126 may be reduced to reduce energy that is available to be dissipated as heat.

The control system 140 may determine a frequency sweep range over which to perform the frequency sweep based on an alignment relationship detected by the sensing system 128. The control system 140 may cause the primary coil 126 to receive signals having frequencies within the frequency sweep range during the frequency sweep. The control system 140 may select the frequency of the charging signal based on a detected alignment relationship (e.g., between a voltage corresponding to the signal applied to the primary coil 126 and at least one of a current corresponding to the signal and a component voltage at a component of the circuit 122) based on the information indicative of the value of the electrical property received from the implantable medical device 102, or based on the detected alignment relationship and the information indicative of the value of the electrical property.

In operation, the control system 140 may perform an initial frequency sweep to identify the resonant frequency of the circuit 122. The initial frequency sweep may be relatively broad (i.e., may cover a relatively large range of frequencies). The initial frequency sweep may also or in the alternative be used to determine an approximate shape of a load voltage to frequency curve of the circuit 122. A step size to be used for subsequent frequency sweeps may be selected based on the approximate shape of a load voltage to frequency curve of the circuit 122, as described further with reference to FIG. 3.

To charge the battery 112, the external charging system 100 may iteratively apply the charging signal to the primary coil 126 (wherein the charging signal is at the charging frequency and the charging signal is applied at a relatively high duty cycle) to charge that battery 112 and search for a new charging frequency using signals having a relatively low duty cycle. To illustrate, the control system 140 may apply a first signal to the primary coil 126. The sensing system 128 may detect an alignment relationship at the circuit 122 responsive to the first signal. Based on the alignment relationship, the control system 140 may determine a frequency sweep range and perform the frequency sweep by applying a second signal to the primary coil 126. The second signal may have a relatively low duty cycle as compared to the charging signal, to the primary coil 126. The sensing system 128 may detect the alignment relationship at the circuit 122 during the frequency sweep. Additionally or in the alternative, the receiver 134 may receive the information indicative of the measured electrical property of the implantable medical device 102 from the measurement system 132. In response to the alignment relationship, the measured electrical property, or both, the control system 140 may select the charging frequency of the charging signal. The control system 140 may apply the charging signal to the primary coil 126 at the selected charging frequency. The charging signal may also be applied at a higher duty cycle than was used for the signals applied to the primary coil 126 during the frequency sweep. In response to detecting a changed condition, the control system 140 may perform another frequency sweep to select a new charging frequency.

The changed condition may correspond to a change in the alignment relationship detected by the sensing system 128, a change in the measured electrical property received by the receiver 134, or both.

Thus, the external charging system 100 may enable external recharging of the battery 112 of the implantable medical device 102 in a manner that reduces heating of the conductive housing 110. In one embodiment, control of the recharging can be performed externally, responsive to information sensed at the external charging system 100. In another embodiment, control of the recharging can be performed externally, responsive to information sensed at the external charging system 100 and in response to information received from the implantable medical device 102. Heating due to recharging the battery 112 can also be reduced by reducing total energy available to be dissipated when impedance is relatively high (e.g., when the signal applied to the primary coil 126 is not at the resonant frequency of the circuit 122) by reducing the duty cycle of the signal. A rate of recharging of the battery 112 can be increased with little or no increase in the heat dissipation by increasing the duty cycle when the impedance is relatively low.

Figure 2:
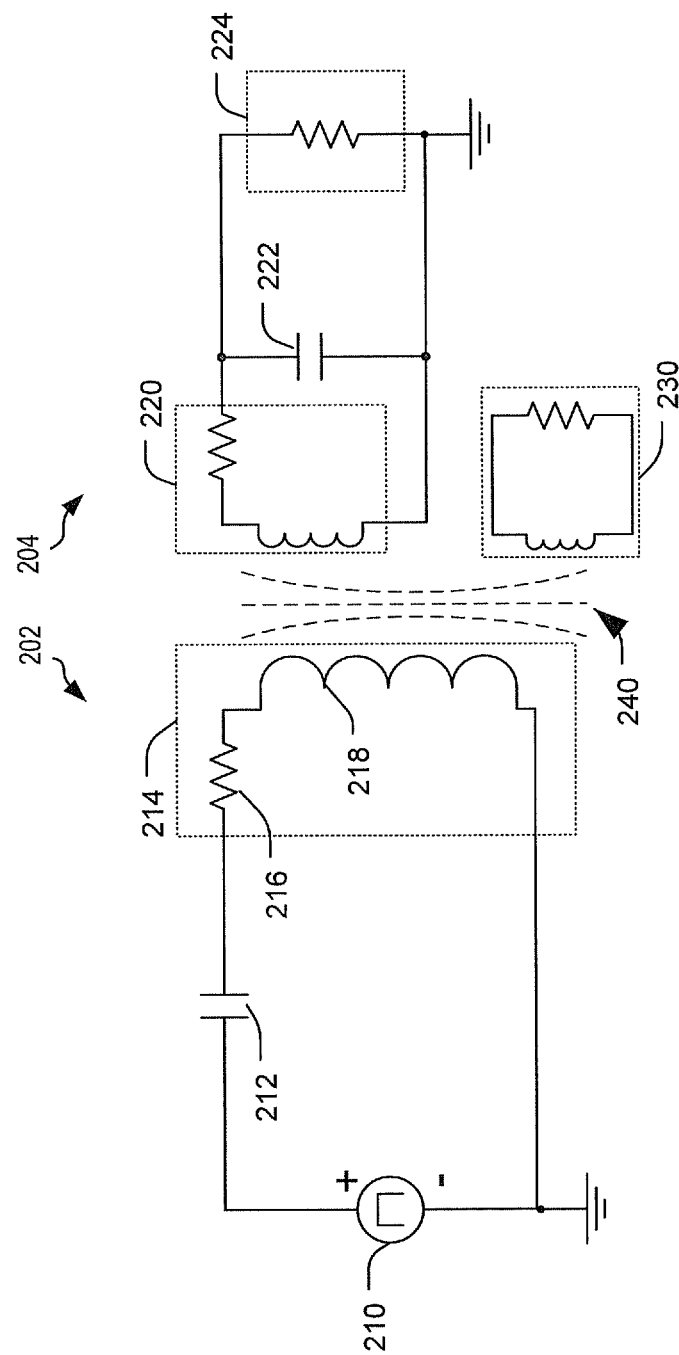
FIG. 2 is a simplified circuit diagram of a particular embodiment of an implantable medical device and a charging system.

FIG. 2 is a simplified circuit diagram of a particular embodiment of an implantable medical device and a charging system. In particular, the simplified circuit diagram illustrates an external charging circuit 202 that is inductively coupled 240 to an internal system, such as an implantable medical device 204. Power may be transferred from the external charging circuit 202 to the implantable medical device 204 to recharge a power source of the implantable medical device 204 via the inductive coupling 240. In a particular embodiment, the external charging circuit 202 may include or be included within the external charging system 100 of FIG. 1. Further, the implantable medical device 204 may include or be included within the implantable medical device 102 of FIG. 1.

In a particular embodiment, the implantable medical device 204 includes a secondary coil 220, a rechargeable power supply 222 (such as a battery, a capacitor, or another energy storage device) and a load 224. For example, the rechargeable power supply 222 may include or be included within the battery 112 of the FIG. 1. The load 224 may include components of the implantable medical device 204 that provide sensing, treatment, communication, other functions of the implantable medical device 204, or any combination thereof. To illustrate, the load 224 may include or be included within the electrodes 108, the controller 116, or the measurement system 132 of FIG. 1. The load 224 may also, or in the alternative, include components that provide other functions of the implantable medical device 204, such as a receiver, a transmitter, or a transceiver (not shown) that facilitates communication between the implantable medical device 204 and the external charging circuit 202; a power treatment system (e.g., a rectifier) (not shown); and so forth. The implantable medical device 204 may include a conductive housing 230. The conductive housing 230 is illustrated separately from the implantable medical device 204 to illustrate the inductive coupling 240 of the primary coil 214 with the conductive housing 230.

The external charging circuit 202 may include a power supply 210, a capacitor 212, and primary coil 214. For example, the external charging circuit 202 may be a portion of the external charging system 100 of FIG. 1. As shown in FIG. 2, the primary coil 214 may exhibit resistance (illustrated in the simplified circuit diagram as a resistor 216) and inductance (illustrated in the simplified circuit diagram as an inductor 218). Thus, the external charging circuit 202 may include or may be modeled as a resistive (R), inductive (L), and capacitive (C) circuit (also referred to as an "RLC circuit"). An RLC circuit has a resonant frequency, which corresponds to a frequency at which impedance due to inductance and impedance due to capacitance cancel each other out, and the RLC circuit exhibits only resistive losses. The resonant frequency is thus an efficient frequency at which to operate the RLC circuit since losses due to impedance and capacitance are reduced. Another characteristic of the resonant frequency of an RLC circuit is that, at the resonant frequency, current and voltage of a signal applied to the RLC circuit are in phase.

When the external charging circuit 202 is inductively coupled 240 to the implantable medical device 204, the inductive coupling 240 affects characteristics of the external charging circuit 202. For example, the primary coil 214 may exhibit a different effective inductance as a result of the inductive coupling 240. To illustrate, when the external charging circuit 202 is remote from the implantable medical device 204 (i.e., no inductive coupling 240 between the external charging circuit 202 and the implantable medical device 204), the external charging circuit 202 may have a first resonant frequency. The first resonant frequency may be a function of capacitance, resistance and inductance of components of the external charging circuit 202, as represented by the capacitor 212, the resistor 216, and the inductor 218, respectively, in FIG. 2. However, when the external charging circuit 202 is proximate to the implantable medical device 204, the external charging circuit 202 and the implantable medical device 204 may be inductively coupled 240, and the external charging circuit 202 may have a second resonant frequency that is different than the first resonant frequency. The second resonant frequency may be a function of the components of the external charging circuit 202 (e.g., the capacitor 212, the resistor 216 and the inductor 218) and a function of the inductive coupling 240. For example, interaction with the secondary coil 220 via the inductive coupling 240 may modify the effective inductance of the inductor 218. To illustrate, the secondary coil 220 may induce a current in the primary coil 214 that opposes a current in the external charging circuit 202, effectively increasing impedance of the inductor 218.

Furthermore, the extent to which the characteristics of the external charging circuit 202 are modified by the inductive coupling 240 may vary depending on a strength of the inductive coupling 240. For example, the inductive coupling 240 may be stronger when the primary coil 214 and the secondary coil 220 are closer to one another and weaker when the primary coil 214 and the secondary coil 220 are further from one another. In another example, the strength of the inductive coupling 240 may vary depending on relative orientation of the primary coil 214 and the secondary coil 220. Thus, rotating or translating the primary coil 214, the secondary coil 220, or both, may change the strength of the inductive coupling 240.

As explained above, the external charging circuit 202 may be a component of a hand-held or portable charging device. Thus, the external charging circuit 202 may be subject to movement as a result of movement of the charging device. Further, the implantable medical device 204 may be subject to movement as a result of movement of the patient, such as shifting in a seat or respiration. Accordingly, the resonant frequency of the external charging circuit 202 may be relatively dynamic due to changes in the inductive coupling 240 between the external charging circuit 202 and the implantable medical device 204.

When a signal applied to the external charging circuit 202 by the power supply 210 is at the resonant frequency of the external charging circuit 202, losses may be reduced as compared to when the signal applied to the external charging circuit 202 is not at the resonant frequency of the external charging circuit 202. Energy that is "lost" from the signal applied to the external charging circuit 202 is lost as heat. Thus, increased energy losses may lead to increased heat generation at the external charging circuit 202, at the implantable medical device 204, at that conductive housing 230, or all three. For safety and health of the patient in which the implantable medical device 204 is implanted, a heat increase of the conductive housing 230 during charging of the rechargeable power supply 222 may be constrained. For example, the conductive housing 230 may be allowed to change temperature by no more than a threshold temperature change during charging of the rechargeable power supply 222. The threshold temperature change may be determined such that tissue surrounding the conductive housing 230 is not harmed or caused discomfort by the heating. For example, the threshold temperature change may be less than 5 degrees Fahrenheit, such as 4 degrees Fahrenheit, 3 degrees Fahrenheit, 2 degrees Fahrenheit, 1 degree Fahrenheit or less than 1 degree Fahrenheit. As explained above, heating losses (and therefore temperature increase of the conductive housing 230) may be reduced by applying a signal from the power supply 210 at the resonant frequency of the external charging circuit 202.

Additionally, energy that is lost to heat is not available to recharge the rechargeable power supply 222. Thus, time required to charge the rechargeable power supply 222 may be reduced when the power supply 210 applies a signal at the resonant frequency of the external charging circuit 202 to the external charging circuit 202 while recharging the rechargeable power supply 222. Reducing the charging time of the rechargeable power supply 222 may improve patient satisfaction with the implantable medical device 204. Additionally, reducing the charging time may improve patient compliance with recharging the rechargeable power supply 222.

During recharging, the power supply 210 may apply a first signal to the external charging circuit 202. A sensing system, such as the sensing system 128 of FIG. 1, may determine whether the first signal applied by the power supply 210 is at the resonant frequency of the external charging circuit 202. For example, the sensing system may determine a first alignment difference between a voltage corresponding to the first signal and a current corresponding to the first signal. In another example, the sensing system may determine a first alignment difference between a voltage corresponding to the first signal and a component voltage at a component of a primary coil circuit, as described in more detail below. The first alignment difference may be a phase difference or a timing difference, as described in more detail below.

When the first alignment difference satisfies a threshold, the first signal may be considered to be sufficiently close to the resonant frequency and charging of the rechargeable power supply 222 may proceed. In a particular embodiment, a duty cycle of the first signal may be changed when the threshold is satisfied to speed up the charging of the rechargeable power supply 222. For example, the duty cycle may be increased while the frequency of the first signal remains constant. Increasing the duty cycle increases an amount of energy that may be transferred via the inductive coupling 240 during a particular time period. In a particular embodiment, a lower duty cycle of the first signal may be used when the first signal is not at the resonant frequency of the external charging circuit 202. The duty cycle of the first signal may be increased to a high duty cycle when the first signal is at the resonant frequency. Since less power is available to be lost to heat at the lower duty cycle, operating at a different duty cycle depending on whether the first signal is at the resonant frequency or not may further reduce heating of the conductive housing 230.

When the first alignment difference fails to satisfy the threshold, the first signal is considered to not be sufficiently close to the resonant frequency of the external charging circuit 202. Accordingly, a search may be performed to identify the resonant frequency. The first alignment difference may provide information regarding a direction and a distance between the first frequency and the resonant frequency, as described in more detail below. In a particular embodiment, a frequency sweep may be performed to identify the resonant frequency. A range over which the frequency sweep is conducted (referred to as the frequency sweep range) may be determined based on the first alignment difference. For example, a difference between the first frequency and a predetermined point of the frequency sweep range (e.g., a starting point of the frequency sweep, a midpoint of the frequency sweep, an ending point of the frequency sweep, or another point of the frequency sweep) may be determined based on a magnitude of the first alignment difference.

After the resonant frequency is determined using the frequency sweep, the power supply 210 may apply a charging signal to the external charging circuit 202. The charging signal has a charging frequency that is substantially equal to the determined resonant frequency. Additionally, a duty cycle of charging signal may be increased relative to the first signal.

During charging of the rechargeable power supply 222, additional frequency sweeps may be performed. For example, frequency sweeps may be performed periodically, based on a predetermined timing. Additionally or in the alternative, a frequency sweep may be performed in response to a detected event. For example, a frequency sweep may be performed when a sensed alignment difference (e.g., a timing difference or a phase difference) fails to satisfy a threshold (e.g., when the signal being applied to the primary coil 214 is determined to be more than a threshold distance from the resonant frequency). In another example, a frequency sweep may be performed in response to a signal received from the implantable medical device 204. To illustrate, the implantable medical device 204 may include a measurement system, such as the measurement system 132 of FIG. 1. The measurement system may measure an electrical property of a charging circuit of the implantable medical device 204. The measurement system may output information indicative of or related to a value of the electrical property. The frequency sweep may be performed in response to the information. To illustrate, the measurement system may measure a charging voltage applied to the rechargeable power supply 222 from the secondary coil 220, and a frequency sweep may be performed when the charging voltage is below a threshold.

Thus, the external charging circuit 202 and the implantable medical device 204 may be operated to reduce heating of the conductive housing 230 and to improve a charge time of the rechargeable power supply 222. Additionally, changes that affect the resonant frequency of the external charging circuit 202, e.g., due to movement, may be accounted for to improve charging and reduce heating. Further, cost and maintenance of the implantable medical device 204 can be reduced, since sensing can be performed externally at the external charging circuit 202.

Figure 3:
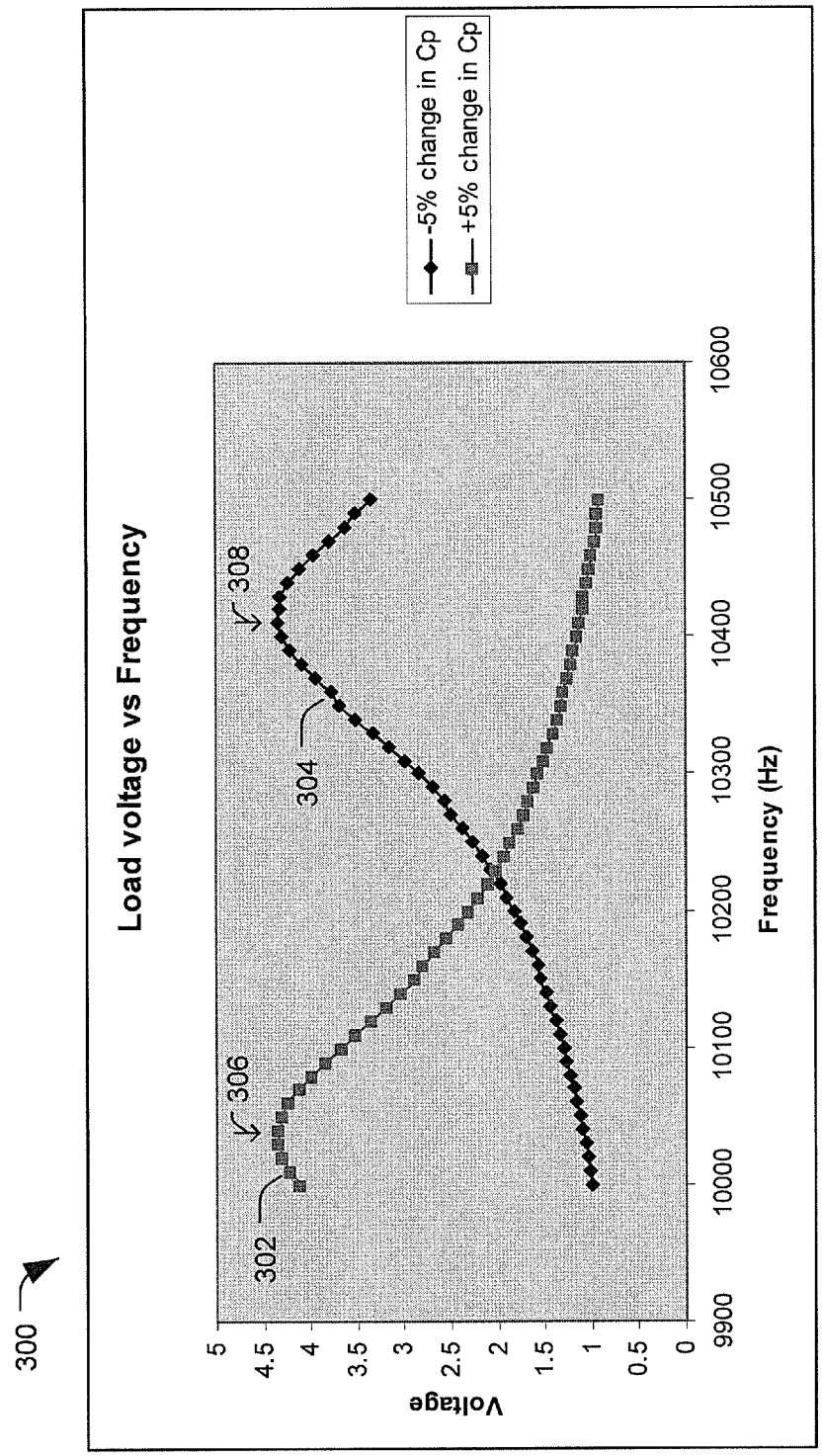
FIG. 3 is a chart of load voltage and frequency for two frequency sweeps that are simulated for a particular embodiment of a system to charge an implantable medical device.

FIG. 3 is a chart 300 of load voltage and frequency for two frequency sweeps that are simulated for a particular embodiment of a system to charge an implantable medical device. In particular, the chart 300 illustrates simulated load voltage measurements at various frequencies during two frequency sweeps for an external charging circuit, such as the external charging circuit 202 of FIG. 2. The chart 300 includes a first series of measurements 302 when a capacitor of the external charging circuit, such as the capacitor 212, has a first capacitance value and a second series of measurements 304 when the capacitor has a second capacitance value. A peak 306 of the first series of measurements 302 corresponds to a resonant frequency of the external charging circuit when the capacitor has the first capacitance value. Similarly, a peak 308 of the second series of measurements 304 corresponds to a resonant frequency of the external charging circuit when the capacitor has the second capacitance value.

To generate the results shown in the chart 300, a nominal capacitance value was selected. The first capacitance value is the nominal capacitance value minus 5 percent and the second capacitance value is the nominal capacitance value plus 5 percent. Thus, the first capacitance value and the second capacitance value simulate a range of variation for a capacitor rated to be within plus or minus 5 percent of its nominal capacitance value. As the chart 300 shows, a plus or minus 5 percent variation in the capacitance value of the capacitor can cause considerable shift in the resonant frequency of the circuit. Thus, an initial frequency sweep of an external charging circuit may be performed to identify a resonant frequency of the external charging circuit. The initial frequency sweep may be relatively broad (i.e., may cover a relatively large range of frequencies), as compared to the frequency sweeps described with reference to FIG. 2.

The initial frequency sweep or another frequency sweep (e.g., a pre-tuning frequency sweep that is performed when the external charging circuit is not in use to charge a power supply of an implantable medical device) may be used to estimate a step size for a subsequent frequency sweep. For example, the second series of measurements 304 indicates an approximate shape of a load voltage to frequency curve of the circuit when the capacitor has the second capacitance value. Based on the shape of the load voltage to frequency curve, a step size of the subsequent frequency sweep can be selected to reduce a likelihood of missing the peak 308. To illustrate, a frequency sweep step size of 500 Hz may be too large, based on the chart 300, since the peak 308 is narrower than 500 Hz. The second series of measurements 304 has a step size of approximately 10 Hz. At the 10 Hz frequency sweep step size, the peak 308 is identifiable. Thus, the 10 Hz frequency step size may be more appropriate than a 500 Hz frequency sweep step size. Other sizes may also be appropriate. For example, it may be desirable to reduce the total number of steps in the frequency sweep in order to decrease an amount of time required to perform the frequency sweep. Accordingly, a frequency sweep step size greater than 10 Hz may be selected so long as the peak 308 can be approximated based on results of the frequency sweep. The initial frequency sweep or pre-tuning frequency sweep may have a relatively small frequency sweep step size in order to map the load voltage to frequency curve so that an appropriate frequency sweep step size can be determined for subsequent frequency sweeps.

FIGS. 4-13 are diagrams illustrating particular embodiments of waveforms that may be used during charging of an implantable medical device. Each of the diagrams shows amplitude versus time for several parameters (such as input voltage, voltage across a component, and current) that may be measured at an external charging circuit, such as the circuit 122 of FIG. 1 or the external charging circuit 202 of FIG. 2. The diagrams illustrate various methods of identifying an alignment difference that may result when a signal applied to the external charging circuit is at an input frequency that is not the resonant frequency of the external charging circuit. The diagrams also illustrate methods of estimating a direction and a distance between the input frequency and the resonant frequency.

Figure 4:
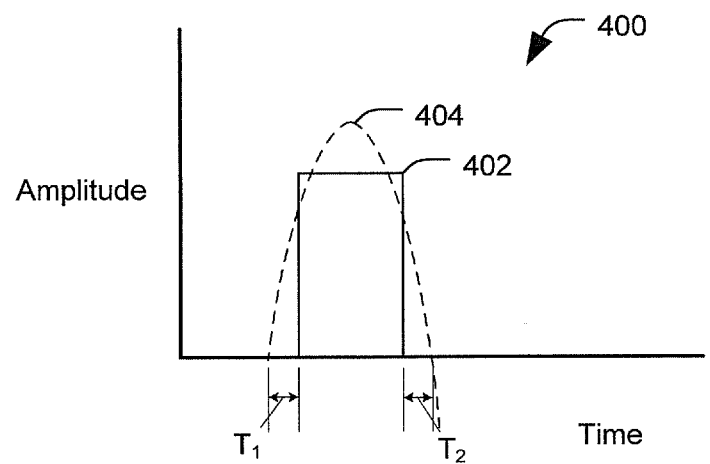
FIGS. 4-13 are diagrams illustrating particular embodiments of waveforms that may be used during charging of an implantable medical device.

Referring to FIG. 4, a diagram 400 of portions of an input voltage waveform 402 and a current waveform 404 at an external charging circuit are shown. The input voltage waveform 402 is shown in FIG. 4 as a square wave; however, other input waveforms may be used, as described further with reference to FIG. 5. An alignment difference between the waveforms 402 and 404 may be determined based on the diagram 400. The alignment difference may be indicative of the direction and distance from the input frequency to the resonant frequency of the external charging circuit.

In FIG. 4, the alignment difference may be determined by determining a first time difference, T1, between a point at which the current waveform 404 has a reference current value (e.g., zero) and a point at which the input voltage waveform 402 has a reference voltage value (e.g., zero). A second time difference, T2, may be determined between a next point of the current waveform 404 that has the reference current value and a next point of the input voltage waveform 402 that has the reference voltage value. The alignment difference may be determined by comparing the first time difference, T1, to the second time difference, T2. To illustrate, when T1 is equal to T2, there is no alignment difference. That is, the current waveform 404 and the input voltage waveform 402 are in phase. When T1 is not equal to T2, the current waveform 404 and the input voltage waveform 402 are out of phase, and the frequency of the input voltage waveform 402 is not the resonant frequency of the external charging circuit.

Figure 5:
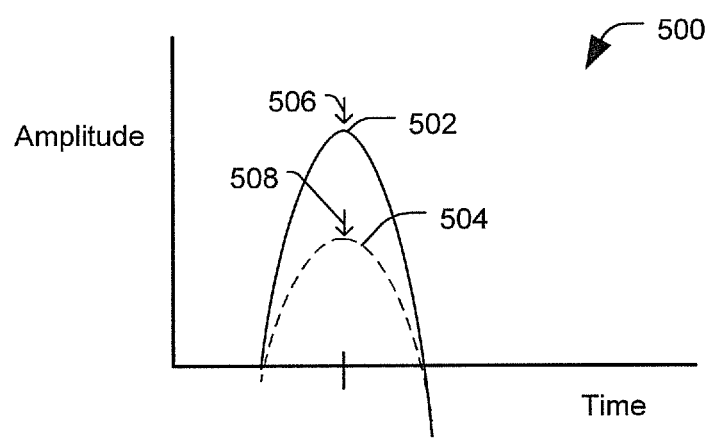

Referring to FIG. 5, a diagram 500 of portions of an input voltage waveform 502 and a current waveform 504 at an external charging circuit are shown. The input voltage waveform 502 is shown in FIG. 5 as a sine wave; however, other input waveforms may be used, such as the square wave of FIG. 4.

An alignment difference between the waveforms 502 and 504 may be determined based on the diagram 500. As explained above, the alignment difference may be indicative of the direction and distance from the input frequency to the resonant frequency of the external charging circuit. As illustrated in FIG. 5, the input voltage waveform 502 has a peak value 506 at a first time. The current waveform 504 also has a peak value 508. In the embodiment illustrated in FIG. 5, the peak value 508 of the current waveform coincides with the peak value 506 of the input voltage waveform 502. Accordingly, in the diagram 500, the input voltage waveform 502 and the current waveform 504 are aligned or in phase, and the frequency of the input voltage waveform 502 is the resonant frequency of the external charging circuit. However, when the peak value 508 of the current waveform 504 and the peak value 506 of the input voltage waveform 502 do not coincide, a time difference between occurrence of each of the peak values 506 and 508 may be indicative of the direction and distance from the frequency of the input voltage waveform 502 to the resonant frequency of the external charging circuit.

Figure 6:
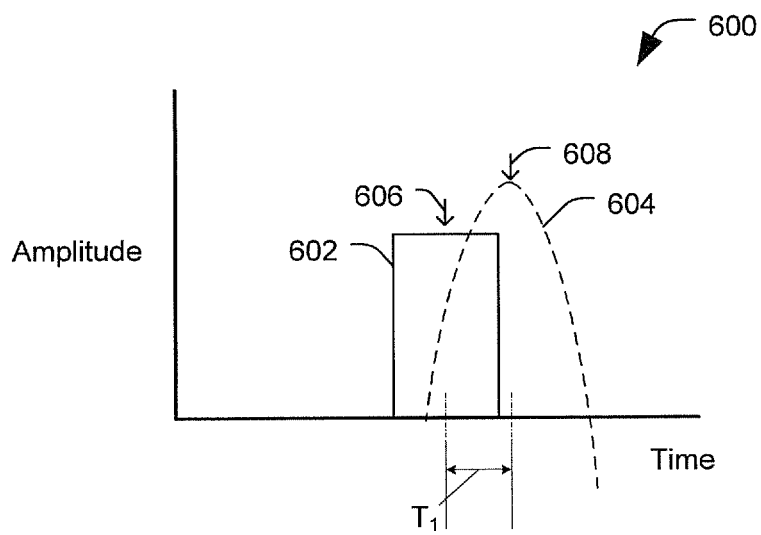

Referring to FIG. 6, a diagram 600 of a portion of an input voltage waveform 602 and a portion of a current waveform 604 at an external charging circuit are shown. The input voltage waveform 602 is illustrated as a square wave. When the input voltage waveform 602 is a square wave, a center point of a square wave pulse may be used as the peak value 606 of the input voltage waveform 602. In FIG. 6, the peak value 606 of the input voltage waveform and the peak value 608 of the current waveform 604 occur at different times. Accordingly, the input voltage waveform 602 and the current waveform 604 are out of alignment (i.e., out of phase) indicating that the frequency of the input voltage waveform 602 is not at the resonant frequency of the circuit.

The time difference, T1, may indicate a distance and a direction from the frequency of the input voltage waveform 602 to the resonant frequency of the circuit. For example, a sign of the time difference, T1, may be negative when the frequency of the input voltage waveform 602 is below the resonant frequency of the circuit and may be positive when the frequency of the input voltage waveform 602 is above the resonant frequency of the circuit. Alternatively, if the reference points are reversed to determine the difference, T1, the sign of the time difference, T1, may be positive when the frequency of the input voltage waveform 602 is below the resonant frequency of the circuit and may be negative when the frequency of the input voltage waveform 602 is above the resonant frequency of the circuit. Further, a magnitude of the time difference, T1, may be proportional to a distance between the frequency of the input voltage waveform 602 and the resonant frequency of the circuit. That is, the magnitude of the time difference, T1, may be larger when the distance between the frequency of the input voltage waveform 602 and the resonant frequency of the circuit is larger and may be smaller when the distance between the frequency of the input voltage waveform 602 and the resonant frequency of the circuit is smaller. Accordingly, an approximate change to the frequency of the input voltage waveform 602 in order to achieve resonance can be estimated based on the sign and magnitude of the time difference, T1.

Figure 7:
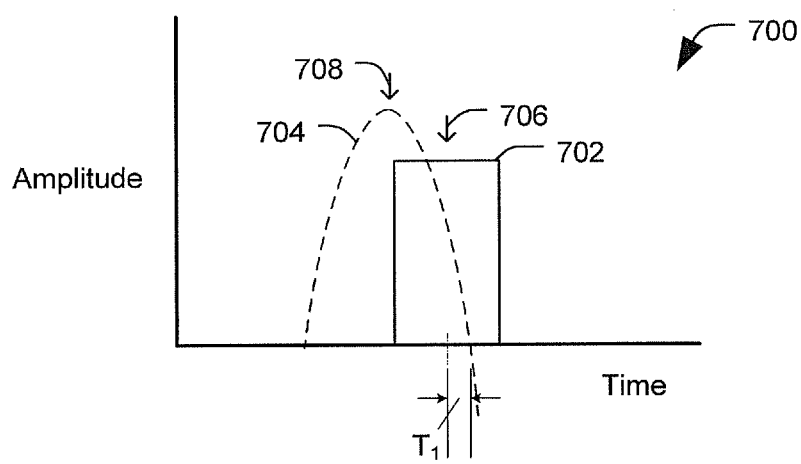

Referring to FIG. 7, a diagram 700 of a portion of an input voltage waveform 702 and a portion of a current waveform 704 at an external charging circuit are shown. The current waveform 704 has a peak value 708, and since the input voltage is a square wave, a center of a pulse of the input voltage waveform 702 may be used as a peak value 706 of the input voltage waveform 702. FIG. 7 illustrates using a time difference between different portions of related waveforms to determine alignment of the waveforms. For example, a time difference, T1, may be determined between the peak value 706 of the input voltage waveform 702 and a point at which the current waveform 704 has a reference current value (e.g., zero). The time difference, T1, may be indicative of the direction and distance from the frequency of the input voltage waveform 702 to the resonant frequency of the external charging circuit. In FIG. 7, the peak value 706 of the input voltage waveform 702 and the peak value 708 of the current waveform 704 are out of alignment (i.e., out of phase) indicating that the input voltage waveform 702 is not at the resonant frequency of the circuit.

The point at which the current waveform 1704 is at the reference current value may lead or lag the peak value 706 of the input voltage waveform 702 by a predetermined amount when the frequency of the input voltage waveform 702 is at the resonant frequency of the circuit. A magnitude of the predetermined amount may depend, for example on the design of the circuit and the reference current value that is used). Thus, a difference between the predetermined amount and the time difference, T1, may indicate a distance and a direction from the frequency of the input voltage waveform 702 to the resonant frequency of the circuit. For example, a sign of the difference between the predetermined amount and the time difference, T1, may be negative when the frequency of the input voltage waveform 702 is below the resonant frequency of the circuit and may be positive when the frequency of the input voltage waveform 702 is above the resonant frequency of the circuit. Alternatively, if the reference points are reversed to determine the time difference, T1, the sign of the difference between the predetermined amount and the time difference, T1, may be positive when the frequency of the input voltage waveform 702 is below the resonant frequency of the circuit and may be negative when the frequency of the input voltage waveform 702 is above the resonant frequency of the circuit. Further, a magnitude of the difference between the predetermined amount and the time difference, T1, may be proportional to a distance between the frequency of the input voltage waveform 702 and the resonant frequency of the circuit. That is, the magnitude of the difference may be larger when the distance between the frequency of the input voltage waveform 702 and the resonant frequency of the circuit is larger, and may be smaller when the distance between the frequency of the input voltage waveform 702 and the resonant frequency of the circuit is smaller. Accordingly, an approximate change to the frequency of the input voltage waveform 702 in order to achieve resonance can be estimated based on the magnitude of the time difference, T1, a sign of the time difference, T1, and information about the predetermined amount that the current waveform 704 leads or lags the input voltage waveform 702 at resonance.

Figure 8:
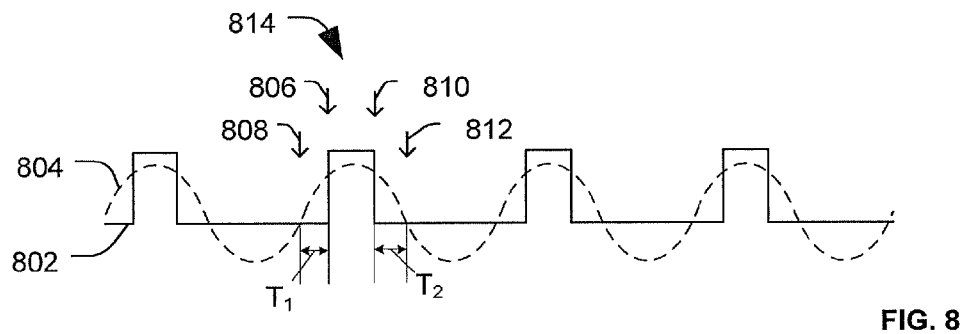
Figure 9:
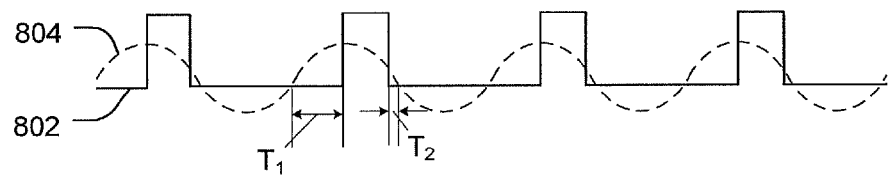
Figure 10:
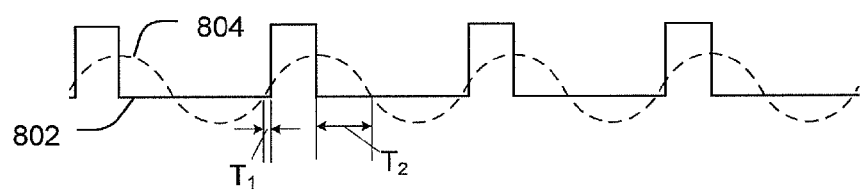

FIGS. 8-10 are diagrams illustrating particular embodiments of waveforms that may be used during charging of an implantable medical device. In particular, FIGS. 8-10 illustrate determining an alignment difference between an input voltage waveform 802 and a current waveform 804. In FIGS. 8-10, the input voltage waveform 802 is illustrated as a square wave; however, as explained above, any waveform shape may be used. An alignment difference between the waveforms 802 and 804 may be determined based on time differences related to each of the waveforms 802, 804. For example, the alignment difference may be determined by comparing a first time difference, T1, and a second time difference, T2. The first time difference, T1, may correspond to a time difference between when the input voltage waveform 802 has a reference voltage value and when the current waveform 804 has a reference current value. The second time difference, T2, may correspond to a time difference between a subsequent occurrence of the input voltage waveform 802 having the reference voltage value and subsequent occurrence of the current waveform 804 having the reference current value.

Referring to FIG. 8, the time differences, T1 and T2, may be time differences between detectable portions of or points of the waveforms 802 and 804. For example, the detectable portions or points of the waveforms 802 and 804 may occur when the waveforms 802 and 804 attain, leave or return to reference values. That is, a detectable portion of or point of the input voltage waveform 802 may correspond to when the input voltage waveform 802 attains, leaves or returns to the reference voltage value, and a detectable portion of or point of the current waveform 804 may correspond to when the current waveform 804 attains, leaves or returns to the reference current value. To illustrate, when the input voltage waveform 802 is a square wave input voltage, as illustrated in FIG. 8, when a first pulse 814 is applied, the input voltage waveform 802 may leave the reference voltage value (e.g., zero or another baseline value) at a first point 806, and when the first pulse 814 end, the input voltage waveform 802 may return to the reference voltage value at a second point 810. Likewise, a detectable point of the current waveform 804 may correspond to when the current waveform 804 crosses the reference current value (e.g., zero or another value), such as at a third point 808, and when the current waveform 804 returns to the reference current value, such as at a fourth point 812. In FIG. 8, the points 810 and 812 are shown as related to a next time that the waveforms 802 and 804 attain their respective reference values; however, the points 810 and 812 may correspond to a subsequent portion of the waveforms 802 and 804. To illustrate, the second point 810 and the fourth point 812 may be measured or detected with respect to a pulse other than the first pulse 814.

Thus, the first time difference, T1, may correspond to a time difference between the third point 808 and the first point 806. The second time difference, T2, may correspond to a time difference between the second point 810 and the fourth point 812. When the first time difference, T1, is substantially equal to the second time difference, T2, as illustrated in FIG. 8, the input voltage waveform 802 and the current waveform 804 are substantially aligned, which is an indication that a frequency of the input voltage waveform 802 is approximately a resonant frequency of a circuit to which the input voltage waveform 802 is applied.

When the first time difference, T1, is larger than the second time difference, T2, as illustrated in FIG. 9, the current waveform 804 is leading the input voltage waveform 802. The current waveform 804 may lead the input voltage waveform 802 when the frequency of the input voltage waveform 802 is below the resonant frequency of the circuit. Further, a magnitude of the difference between the first time difference, T1, and the second time difference, T2, may be proportional to a distance between the frequency of the input voltage waveform 802 and the resonant frequency of the circuit. That is, the magnitude of the difference between the first time difference, T1, and the second time difference, T2, may be larger when the distance between the frequency of the input voltage waveform 802 and the resonant frequency of the circuit is larger, and may be smaller when the distance between the frequency of the input voltage waveform 802 and the resonant frequency of the circuit is smaller. Accordingly, an approximate change to the frequency of the input voltage waveform 802 in order to achieve resonance can be estimated based on the magnitude of the difference between the first time difference, T1, and the second time difference, T2, and based on whether T1 or T2 is larger.

When the first time difference, T1, is smaller than the second time difference, T2, as illustrated in FIG. 10, the input voltage waveform 802 is leading the current waveform 804. The input voltage waveform 802 may lead the current waveform 804 when the frequency of the input voltage waveform 802 is above the resonant frequency of the circuit. Further, a magnitude of the difference between the first time difference, T1, and the second time difference, T2, may be proportional to a distance between the frequency of the input voltage waveform 802 and the resonant frequency of the circuit.

Thus, by comparing the first time difference, T1, and the second time difference, T2, an alignment difference between the waveforms 802 and 804 can be determined. The alignment difference may be indicative of the direction and distance from the frequency of the input voltage waveform 802 to the resonant frequency of a circuit, such as the external charging circuit 202 of FIG. 2. A frequency sweep range may be selected based on the alignment difference to determine the resonant frequency of the circuit. To illustrate, a direction to change the frequency relative to the frequency of the input voltage waveform 802 may be determined based on a sign of the alignment difference (e.g., a sign of T1−T2). In addition, a magnitude of a frequency change from the frequency of the input voltage waveform 802 to a particular portion of the frequency sweep (e.g. a midpoint of the frequency sweep range) may be selected based on a magnitude of the alignment difference.

Figure 11:
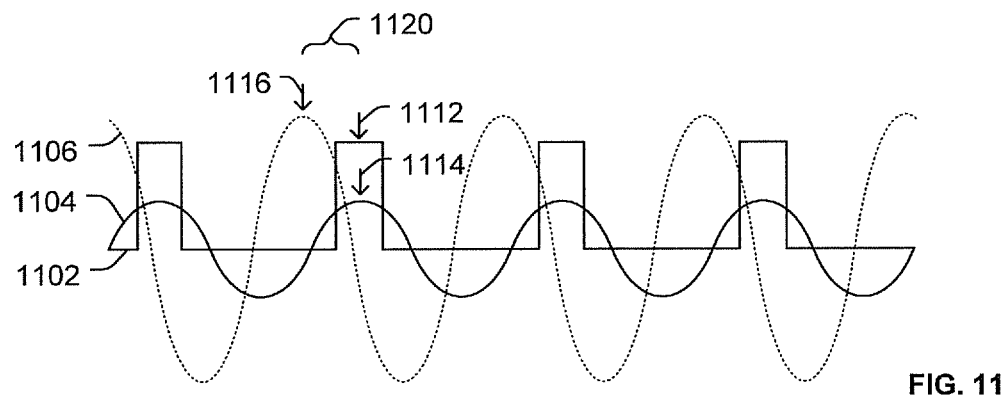
Figure 12:
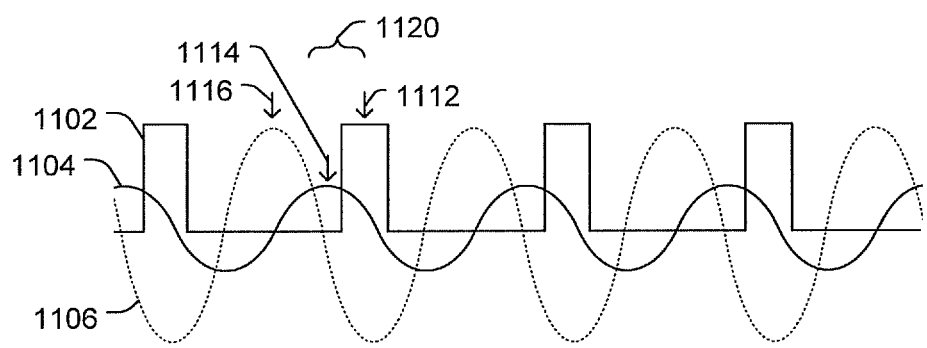
Figure 13:
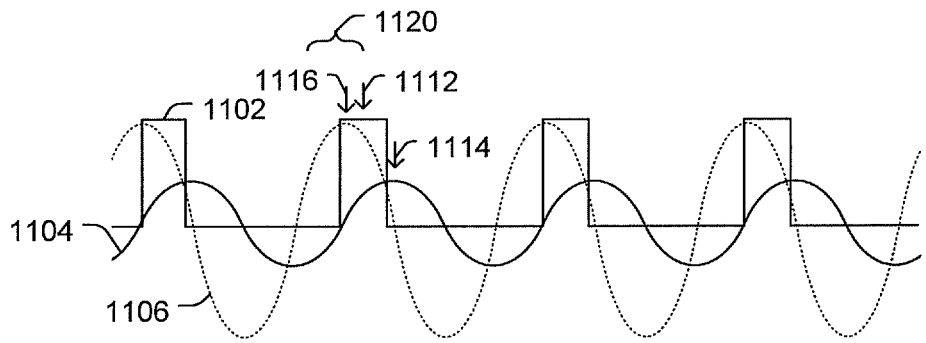

FIGS. 11-13 are diagrams illustrating particular embodiments of waveforms that may be used during charging of an implantable medical device. In particular, FIGS. 11-13 illustrate determining an alignment difference between an input voltage waveform 1102 and one or more other waveforms, such as a current waveform 1104 or a component voltage waveform 1106. For example, the component voltage waveform 1106 may be measured or detected across a capacitor, such as the capacitor 212 of FIG. 2, or across an inductor, such as the inductor 218 of FIG. 2, of a circuit to which the input voltage waveform 1102 is applied. In FIGS. 11-13, the input voltage waveform 1102 is illustrated as a square wave; however, as explained above, any waveform shape may be used.

An alignment difference between the input voltage waveform 1102 and the one or more other waveforms 1104 and 1106 may be determined based on when the waveforms 1102, 1104, 1106 attain, leave or return to particular reference values or undergo detected transitions. For example, the alignment difference may be determined by comparing a time at which the input voltage waveform 1102 has a peak value 1112 and a time at which the current waveform 1104 has a peak value 1114. When the input voltage waveform 1102 is a square wave, the peak value 1112 may correspond to a center point of a pulse. In another example, the alignment difference may be determined by comparing a time at which the input voltage waveform 1102 has the peak value 1112 and a time at which the component voltage waveform 1106 has a peak value 1116. Although peak values 1112, 1114, and 1116 are illustrated in FIGS. 11-13, other points on the waveforms 1102, 1104, 1106 may be used as reference points. To illustrate, a reference point of one or more of the waveforms 1102, 1104, 1106 may be a point at which the waveform has a predetermined reference value or a point at which the waveform undergoes a detectable transition, such as a sign change.

In FIG. 11, the peak value 1112 of the input voltage waveform 1102 is substantially aligned with the peak value 1114 of the current waveform 1104. Accordingly, the input voltage and current of the circuit are aligned (i.e., in phase) indicating that a frequency of the input voltage waveform 1102 is substantially equal to a resonant frequency of the circuit. Additionally, the peak value 1112 of the input voltage waveform 1102 is offset by a predetermined amount 1120 from the peak value 1116 of the component voltage waveform 1106, which is another indicator that the frequency of the input voltage waveform 1102 is substantially equal to a resonant frequency of the circuit. A magnitude and direction of the predetermined amount 1120 of the offset between the peak value 1112 of the input voltage waveform 1102 and the peak value 1116 of the component voltage waveform 1106 depends on the detailed design of the circuit and a type of component across which the component voltage waveform is measured (e.g., a capacitor or an inductor).

In FIG. 12, the peak value 1114 of the current waveform 1104 leads the peak value 1112 of the input voltage waveform 1102. The current waveform 1104 may lead the input voltage waveform 1102 when the frequency of the input voltage waveform 1102 is below the resonant frequency of the circuit. Further, an amount that the current waveform 1104 leads the input voltage waveform 1102 may be proportional to a distance between the frequency of the input voltage waveform 1102 and the resonant frequency of the circuit. Accordingly, an approximate change to the frequency of the input voltage waveform 1102 to achieve resonance can be estimated based on the amount that the current waveform 1104 leads the input voltage waveform 1102.

In FIG. 13, the peak value 1112 of the input voltage waveform 1102 leads the peak value 1114 of the current waveform 1104. The input voltage waveform 1102 may lead the current waveform 1104 when the frequency of the input voltage waveform 1102 is above the resonant frequency of the circuit. Further, an amount that the input voltage waveform 1102 leads the current waveform 1104 may be proportional to a distance between the frequency of the input voltage waveform 802 and the resonant frequency of the circuit. Accordingly, an approximate change to the frequency of the input voltage waveform 1102 to achieve resonance can be estimated based on the amount that the input voltage waveform 1102 leads the current waveform 1104.

Additionally, or in the alternative, the approximate change to the frequency of the input voltage waveform 1102 may be estimated based on an amount of a measured offset between the peak value 1112 of the input voltage waveform 1102 and the peak value 1116 of the component voltage waveform 1106. As previously explained, when the input voltage waveform 1102 is at the resonant frequency of the circuit, the peak value 1112 of the input voltage waveform 1102 may be offset from the peak value 1116 of the component voltage waveform 1106 by the predetermined amount 1120. When the peak value 1112 of the input voltage waveform 1102 is offset from the peak value 1116 of the component voltage waveform 1106 by an actual or measured amount that is more than or less than the predetermined amount 1120, a difference between the predetermined amount 1120 of the offset and the actual or measured amount of the offset may indicate a distance and a direction from the frequency of the input voltage waveform to the resonant frequency of the circuit.

Thus, by comparing timing of occurrence of particular points of the input voltage waveform 1102 and one or more other waveforms, such as the current waveform 1104 or the component voltage waveform 1106, an alignment difference between the waveforms 1102, 1104, 1106 can be determined. The alignment difference may be indicative of the direction and distance from the frequency of the input voltage waveform 1102 to the resonant frequency of the circuit, such as the external charging circuit 202 of FIG. 2. In a particular embodiment, the alignment difference may be used to select a frequency sweep range to determine the resonant frequency of the circuit. To illustrate, a distance from the frequency of the input voltage waveform 1102 to a particular portion of the frequency sweep range (e.g. a starting point, a midpoint, an endpoint or another point within the frequency sweep range) may be selected based on a magnitude of the alignment difference.

Figure 14:
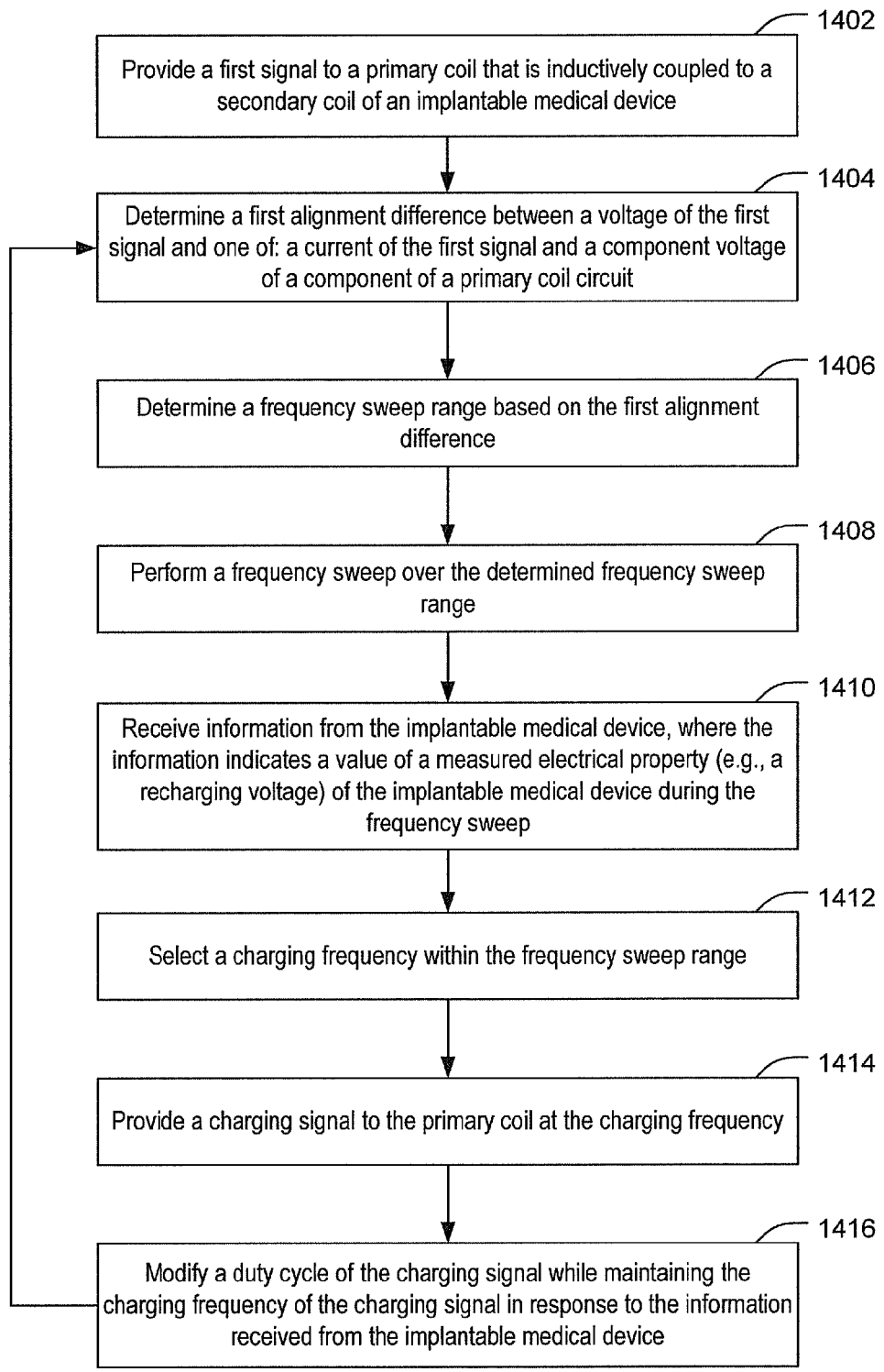
FIG. 14 is flow chart of a particular embodiment of a method of charging an implantable medical device.

FIG. 14 is flow chart of a particular embodiment of a method of charging an implantable medical device. For example, the method may be performed by an external charging system, such as the external charging system 100 of FIG. 1, during charging of an implantable medical device, such as the implantable medical device 102 of FIG. 1. In a particular embodiment, the implantable medical device may include a nerve stimulation device. The nerve stimulation device may include a secondary coil, a battery and a battery charging circuit within a conductive housing. The secondary coil may be responsive to a charging signal applied to the primary coil of an external charging circuit to provide energy to charge the battery. In this particular embodiment, a temperature of the conductive housing may increase no more than a threshold amount during charging of the battery. For example, during charging of the battery, the temperature of the conductive housing may increase by no more than one degree Fahrenheit, by no more than two degrees Fahrenheit, by no more than three degrees Fahrenheit, by no more than four degrees Fahrenheit, by no more than five degrees Fahrenheit, or by no more than another predetermined threshold amount (where the predetermined threshold amount is selected to protect the tissue surrounding the implantable medical device).

The method may include, at 1402, providing a first signal to the primary coil of the external charging system when the primary coil is inductively coupled to the secondary coil of the implantable medical device. For example, the primary coil may include the primary coil 214 of FIG. 2, which is inductively coupled 240 to the secondary coil 220 of the implantable medical device 204. The first signal may include an input voltage waveform, such as the input voltage waveform 402 of FIG. 4, the input voltage waveform 502 of FIG. 5, the input voltage waveform 602 of FIG. 6, the input voltage waveform 702 of FIG. 7, the input voltage waveform 802 of FIGS. 8-10, the input voltage waveform 1102 of FIGS. 11-13, another input waveform, or any combination thereof.

The method may also include, at 1404, determining a first alignment difference between a voltage corresponding to the first signal and at least one of a current corresponding to the first signal and a component voltage at a component of a primary coil circuit (i.e., an external charging circuit). The first alignment difference may include at least one of a phase difference and a time difference. For example, the first alignment difference may be determined by comparing the input voltage waveform 802 and the current waveform 804 of FIGS. 8-10. In another example, the first alignment difference may be determined by comparing timing of the input voltage waveform 1102 and the component voltage waveform 1106 of FIGS. 11-13. A current waveform and a voltage waveform may be generated in response to the first signal being applied to the primary coil. In a particular embodiment, the first alignment difference may be determined by determining a first time difference between a first portion of the current waveform and a corresponding first portion of the voltage waveform and determining a second time difference between a second portion of the current waveform and a corresponding second portion of the voltage waveform. A first phase difference may be determined by comparing the first time difference and the second time difference. In another particular embodiment, the first alignment difference may be determined by determining a first time difference between a point at which the current waveform has a reference current value and a point at which the voltage waveform has a reference voltage value and determining a second time difference between a next point of the current waveform that has the reference current value and a next point of the voltage waveform that has the reference voltage value, as described with reference to FIG. 4. The first phase difference may be determined by comparing the first time difference and the second time difference.

When the first alignment difference indicates that a frequency of the first signal is not a resonant frequency of a circuit coupled to the primary coil, a frequency sweep may be performed, based on the first alignment difference, to find the resonant frequency. For example, the method may include, at 1406, determining a frequency sweep range based on the first alignment difference. The frequency sweep range may correspond to a range of frequencies to be checked to identify the resonant frequency.

The method may also include, at 1408, performing a frequency sweep over the frequency sweep range. The frequency sweep may be performed by applying a series of signals that have frequencies within the frequency sweep range to the primary coil, where the frequencies of adjacent signals in the series are separated by a frequency sweep step size. To illustrate, the frequency sweep may be performed by applying at least one second signal to the primary coil. The first signal may have a first frequency (that is within or outside the frequency sweep range) and the second signal may have a second frequency that is in the frequency sweep range. Subsequent to providing the second signal, a third signal may be provided to the primary coil. The third signal may have a third frequency that is in the frequency sweep range.

In a particular embodiment, a difference between the first frequency of the first signal and a predetermined point of the frequency sweep range (e.g., a beginning point of the frequency sweep, a midpoint of the frequency sweep, an ending point of the frequency sweep, or another point of the frequency sweep) is determined based on a magnitude of the first alignment difference. In a particular embodiment, a frequency sweep step size (e.g., a difference between the second frequency and the third frequency) is determined based on a magnitude of the first alignment difference. In a particular embodiment, a direction between the second frequency and the third frequency (e.g., whether the frequency is increasing or decreasing) is determined based on a sign of the first alignment difference.

In a particular embodiment, the method includes, at 1410, receiving information from the implantable medical device. For example, the information may indicate a value of a measured electrical property of the implantable medical device during the frequency sweep. To illustrate, the information may indicate the value of the measured electrical property of the implantable medical device while the second signal, the third signal or another signal is provided to the primary coil. In a particular illustrative embodiment, the information indicates a recharging voltage applied by a battery charging circuit of the implantable medical device to the battery, where the recharging voltage is responsive to current in the secondary coil. In this case, the measured electrical property is the recharging voltage of the battery charging circuit.

The method may include, at 1412, selecting a charging frequency within the frequency sweep range. In a particular embodiment, the charging frequency may be selected based on the information received from the implantable medical device. For example, the frequency sweep may be performed over a frequency sweep range that is expected to include the resonate frequency of the circuit. A frequency that corresponds to a largest (or smallest) value of the measured electrical property may be selected as the charging frequency. For example, when the measured electrical value is the recharging voltage, a frequency of the frequency sweep range that corresponds to a largest measured value of the recharging voltage may be selected as the charging frequency. Thus, the charging frequency may correspond to a frequency that provides a large recharging voltage, which may lead to faster recharging of the battery than a smaller recharging voltage.

In another particular embodiment, during the frequency sweep, one or more additional alignment differences may be determined. For example, the additional alignment differences may be determined to identify when a frequency of the signal applied to the primary coil is at the resonant frequency of the circuit coupled to the primary coil. To illustrate, during the frequency sweep the second signal and the third signal may be applied to the primary coil. A second alignment difference may be determined between a voltage corresponding to the second signal and at least one of a current corresponding to the second signal and a second component voltage at the component. Additionally, a third alignment difference may be determined between a voltage corresponding to the third signal and at least one of a current corresponding to the third signal and a third component voltage at the component. The charging frequency may be selected within the frequency sweep range based on at least one of the first alignment difference, the second alignment difference and the third alignment difference. The charging frequency may be approximately the resonant frequency of the circuit that includes or is coupled to the primary coil when the frequency sweep is performed. The resonant frequency of the circuit may correspond to a frequency that generates the least amount of heat.

The method may include, at 1414, providing a charging signal at the charging frequency to the primary coil. A duty cycle of the charging signal may be modified while maintaining the charging frequency of the charging signal, at 1416. For example, the duty cycle may be modified in response to the information received from the implantable medical device. In another example, the duty cycle may be changed in response to determining that the charging frequency is approximately the resonant frequency of the circuit that includes or is coupled to the primary coil (i.e., within a threshold). In a particular embodiment, the duty cycle of the charging signal may be larger than a duty cycle of at least one of the first signal, the second signal and the third signal. Reducing the duty cycle for the frequency sweep may reduce an amount of power dissipated as heat. For example, the frequency sweep may be performed over a range of frequencies, most of which are not the resonant frequency of the circuit. Thus, a relatively substantial portion of power transmitted via signals during the frequency sweep may be dissipated as heat due to impedance of the circuit at the frequencies of the signals applied to the circuit during the frequency sweep. Using a relatively low duty cycle for the frequency sweep reduces an amount of power available to be dissipated. However, once the resonant frequency is determined using the frequency sweep, the charging signal may be provided substantially at the resonant frequency. At the resonant frequency, impedance of the circuit is reduced. Accordingly, the duty cycle may be increased, since dissipation due to impedance is reduced.

The method may include performing one or more additional frequency sweeps in response to the information received from the implantable medical device. For example, the method may return to 1404 to determine a second alignment difference and may subsequently perform a second frequency sweep based on the second alignment difference. In another example, the method may include performing a second frequency sweep in response to detecting an alignment difference related to the charging signal that satisfies a threshold. To illustrate, the second frequency sweep may be performed in response to detecting that an alignment difference between a voltage corresponding to the charging signal and a current corresponding to the charging signal satisfies an alignment threshold. In another illustrative example, the second frequency sweep may be performed in response to detecting that an alignment difference between the voltage corresponding to the charging signal and a component voltage at the component satisfies the alignment threshold.

Thus, the method may enable external recharging of the battery of the implantable medical device in a manner that reduces heat dissipation, which may increase a temperature of the conductive housing of the implantable medical device. In one embodiment, control of the recharging can be performed externally, responsive to information sensed at an external charging system. In another embodiment, control of the recharging can be performed externally, responsive to information sensed at the external charging system and based on information received from the implantable medical device. Heating of the implantable medical device due to recharging the battery may also be reduced by reducing the duty cycle of the signal when the signal applied to the primary coil is not at the resonant frequency of the external charging circuit. Reducing the duty cycle of the signal reduces the amount of energy available for heat dissipation. A rate of recharging the battery can be increased with little or no increase in the heat dissipation by increasing the duty cycle when the impedance is relatively low (e.g., when the frequency of the signal applied to the primary coil is the resonant frequency of the circuit).

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. For example, method steps may be performed in a different order than is shown in the figures or one or more method steps may be omitted. Accordingly, the disclosure and the figures are to be regarded as illustrative rather than restrictive.

Moreover, although specific embodiments have been illustrated and described herein, it should be appreciated that any subsequent arrangement designed to achieve the same or similar results may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, the claimed subject matter may be directed to less than all of the features of any of the disclosed embodiments.

What is claimed is:

1. A method comprising:
   providing a first signal to a primary coil that is inductively coupled to a secondary coil of an implantable medical device;
   determining a first alignment difference between a first signal voltage and at least one of a first signal current and a component voltage at a component of a primary coil circuit;
   determining a frequency sweep range based on the first alignment difference; and
   performing a frequency sweep over the frequency sweep range.

2. The method of claim 1, wherein performing the frequency sweep comprises:
   providing a second signal to the primary coil, wherein the first signal has a first frequency and the second signal has a second frequency that is in the frequency sweep range; and
   subsequent to providing the second signal, providing a third signal to the primary coil, wherein the third signal has a third frequency that is in the frequency sweep range.

3. The method of claim 2, wherein a difference between the first frequency of the first signal and a predetermined point of the frequency sweep is determined based on a magnitude of the first alignment difference.

4. The method of claim 2, wherein a difference between the second frequency and the third frequency corresponds to a frequency sweep step size and wherein the frequency sweep step size is determined based on a magnitude of the first alignment difference.

5. The method of claim 2, wherein a direction between the second frequency and the third frequency is determined based on a sign of the first alignment difference.

6. The method of claim 2, further comprising:
receiving first information from the implantable medical device, wherein the first information indicates a value of a measured electrical property of the implantable medical device while the second signal is provided to the primary coil;
receiving second information from the implantable medical device, wherein the second information indicates a second value of the measured electrical property of the implantable medical device while the third signal is provided to the primary coil;
selecting a charging frequency within the frequency sweep range based on at least one of the first information and the second information; and
providing a charging signal at the charging frequency to the primary coil.

7. The method of claim 2, further comprising:
determining a second alignment difference between a second signal voltage and at least one of a second signal current and a second component voltage at the component;
determining a third alignment difference between a third signal voltage and at least one of a third signal current and a third component voltage at the component; and
selecting a charging frequency within the frequency sweep range based on at least one of the first alignment difference, the second alignment difference and the third alignment difference; and
providing a charging signal to the primary coil at the charging frequency.

8. The method of claim 7, wherein a duty cycle of the charging signal is larger than a duty cycle of at least one of the first signal, the second signal and the third signal.

9. The method of claim 7, wherein the charging frequency is approximately a resonant frequency of a circuit that includes the primary coil when the frequency sweep is performed.

10. The method of claim 7, further comprising performing a second frequency sweep in response to a fourth alignment difference between a charging signal voltage and at least one of a charging signal current satisfying a first threshold and a fourth component voltage at the component satisfying a second threshold.

11. The method of claim 7, wherein the implantable medical device comprises a nerve stimulation device, wherein the nerve stimulation device includes the secondary coil, a battery and a battery charging circuit within a conductive housing, wherein the secondary coil is responsive to the charging signal applied to the primary coil to provide energy to charge the battery, and wherein a temperature of the conductive housing increases by no more than two degrees Fahrenheit during charging of the battery.

12. The method of claim 7, further comprising receiving information from the implantable medical device, wherein the information indicates a value of a measured electrical property of the implantable medical device during the frequency sweep.

13. The method of claim 12, wherein the information indicates a voltage applied to a battery charging circuit of the implantable medical device, wherein the voltage is responsive to current in the secondary coil.

14. The method of claim 12, further comprising in response to the information received from the implantable medical device, modifying a duty cycle of the charging signal while maintaining the charging frequency of the charging signal.

15. The method of claim 12, further comprising performing a second frequency sweep in response to the information received from the implantable medical device.

16. The method of claim 1, wherein a current waveform and a voltage waveform are generated in response to the first signal being applied to the primary coil and wherein determining the first alignment difference comprises:
determining a first time difference between a first portion of the current waveform and a corresponding first portion of the voltage waveform;
determining a second time difference between a second portion of the current waveform and a corresponding second portion of the voltage waveform; and
determining a first phase difference by comparing the first time difference and the second time difference.

17. The method of claim 1, wherein a current waveform and a voltage waveform are generated in response to the first signal being applied to the primary coil and wherein determining the first alignment difference comprises:
determining a first time difference between a point at which the current waveform has a reference current value and a point at which the voltage waveform has a reference voltage value;
determining a second time difference between a next point of the current waveform that has the reference current value and a next point of the voltage waveform that has the reference voltage value; and
determining a first phase difference by comparing the first time difference and the second time difference.

18. The method of claim 1, wherein the first alignment difference comprises at least one of a phase difference and a time difference.

19. A device comprising
a primary coil coupled to a circuit and operable to inductively couple to a secondary coil within an implantable medical device to transfer energy to the secondary coil within the implantable medical device responsive to a signal of the circuit;
a sensing system coupled to the circuit, the sensing system operable to detect an indication of an alignment relationship between a signal voltage and at least one of a signal current and a component voltage at a component of the circuit; and
a control system responsive to the sensing system, the control system operable to determine a frequency sweep range based on the alignment relationship and to cause the primary coil to receive the signal having a frequency within the frequency sweep range during the transfer of the energy.

20. The device of claim 19, wherein the primary coil is at least partially contained within a portable housing, and wherein the control system adjusts the frequency of the signal and a duty cycle of the signal in response to a change in an electrical property of the circuit due at least in part to relative motion of the primary coil and the secondary coil.

21. The device of claim 19, further comprising a receiver operatively coupled to the control system, the receiver operable to receive information from the implantable medical device, wherein the information is indicative of an electrical property associated with the implantable medical device or a component of the implantable medical device, and wherein the control system modifies the signal responsive to the information.

22. The device of claim 19, wherein the circuit includes a capacitor and wherein the control system uses the frequency sweep to estimate a resonant frequency of the circuit during the transfer of the energy.

23. A non-transitory computer-readable storage medium storing instructions executable by a computer system to:
cause a first signal to be provided to a primary coil that is inductively coupled to a secondary coil of an implantable medical device;
determine a first alignment difference between a first signal voltage and at least one of a first signal current and a component voltage at a component of a primary coil circuit;
determine a frequency sweep range based on the first alignment difference; and
cause a frequency sweep to be performed over the frequency sweep range.

24. The non-transitory computer readable storage medium of claim 23, wherein the instructions to cause the frequency sweep to be performed comprise instructions to:
cause a second signal to be provided to the primary coil, wherein the first signal has a first frequency and the second signal has a second frequency that is in the frequency sweep range; and
subsequent to causing the second signal to be provided, cause a third signal to be provided to the primary coil, wherein the third signal has a third frequency that is in the frequency sweep range.

25. The non-transitory computer readable storage medium of claim 24, wherein a difference between the first frequency of the first signal and a predetermined point of the frequency sweep is determined based on a magnitude of the first alignment difference.

26. The non-transitory computer readable storage medium of claim 24, wherein a difference between the second frequency and the third frequency corresponds to a frequency sweep step size and wherein the frequency sweep step size is determined based on a magnitude of the first alignment difference.

27. The non-transitory computer readable storage medium of claim 24, wherein a direction between the second frequency and the third frequency is determined based on a sign of the first alignment difference.

* * * * *